US00PP16640P2

(12) United States Plant Patent
Utecht

(10) Patent No.: US PP16,640 P2
(45) Date of Patent: Jun. 13, 2006

(54) *GERANIUM* PLANT NAMED 'FISNIFIRE'

(50) Latin Name: *Pelargonium zonale*
Varietal Denomination: Fisnifire

(75) Inventor: Angelika Utecht, Montabaur (DE)

(73) Assignee: Florfis AG, Binningen (CH)

( * ) Notice: Subject to any disclaimer, the term of this patent is extended or adjusted under 35 U.S.C. 154(b) by 83 days.

(21) Appl. No.: 10/998,631

(22) Filed: Nov. 30, 2004

(51) Int. Cl.
*A01H 5/00* (2006.01)

(52) U.S. Cl. ..... Plt./330
(58) Field of Classification Search ..... Plt./330
See application file for complete search history.

(56) References Cited

PUBLICATIONS

German PBR Application No. PEL 1900 filed Jun. 4, 2003 and withdrawn Oct. 5, 2004 (Copy of German Gazettes dated 1) Jul. 15, 2003—Listing Assigned Application for Protection Number (2 pgs), 2) May 15, 2004—Publishing Proposed Variety Denomination (2 pgs), and 3) Nov. 15, 2004—Listing Withdrawal of Application for Protection (2 pgs)).

Canadian PBR Application No. 03–3906 filed Nov. 21, 2003 (Copy of Canadian Plant Varieties Journal dated Jan., 2004 Listing Assigned Application Number (2 pgs).

Community Plant Variety Office (CPVO) No. 2004/1258 filed Jul. 5, 2004 (Copy of Official Gazette of the CPVO dated Oct. 15, 2004 Listing Assigned Application Number and Variety Denomination (3 pgs).

Fischer 2005 catalogue offering 'Fisnifire' (with shipment of plant material available starting Dec., 2004) (3 pgs).

*Primary Examiner*—Kent Bell
(74) *Attorney, Agent, or Firm*—Foley & Lardner LLP

(57) ABSTRACT

A new and distinct cultivar of *geranium* plant named 'Fisnifire' particularly characterized by the combined features of brilliant, orange-red, single-type flowers, large inflorescences on, dark red peduncles; robust, dark-green foliage with strong zonation; initially fairly compact, but later medium to tall and well-branched plant habit, about medium spring flowering response; good weather resistance and well suited as a robust plant for landscaping.

1 Drawing Sheet

Genus and species of the plant claimed: *Pelargonium zonale* L'Héritier (hybrid).
Variety denomination: 'Fisnifire'.

BACKGROUND OF THE INVENTION

The present invention comprises a new and distinct cultivar of *geranium*, botanically known as *Pelargonium zonale*, and hereinafter referred to by the cultivar name 'Fisnifire'.

'Fisnifire' is a product of a planned breeding program which had the objective of creating new zonal *geranium* cultivars with single-type flowers, zoned foliage, in various colors, and generally suitable for a range of robust outdoor varieties.

'Fisnifire' originated from a hybridization made by the inventor, Angelika Utecht, in a controlled breeding program in Hillscheid, Germany, in 1998. The female parent was the patented variety 'Fishelen' (U.S. Plant Pat. No. 12,727), characterized by semi-double, salmon-pink colored flowers, medium green foliage with strong zonation, and medium sized plant habit. The male parent of 'Fisnifire' was the unpatented plant No. 93-0266-7, characterized by having red, single-type flowers, dark green foliage and fairly vigorous growth habit.

'Fisnifire' was selected as one flowering plant within the progeny of the stated cross by Angelika Utecht in 1999 in a controlled environment in Moncarapacho, Portugal.

The first act of asexual reproduction of 'Fisnifire' was accomplished when vegetative cuttings were taken from the initial selection in the fall of 1999 in a controlled environment in Moncarapacho, Portugal, by, or under the supervision of, Angelika Utecht.

Horticultural examination of plants grown from cuttings of the plant initiated in May of 2000, in Hillscheid, Germany, and continuing thereafter, has demonstrated that the combination of characteristics as herein disclosed for 'Fisnifire' are firmly fixed and are retained through successive generations of asexual reproduction.

BRIEF SUMMARY OF THE INVENTION

'Fisnifire' has not been observed under all possible environmental conditions. The phenotype may vary significantly with variations in environment such as temperature, light intensity and day length. The following observations, measurements, and comparisons describe plants grown in Hillscheid, Germany, under greenhouse conditions which approximate those generally used in commercial practice.

The following traits have been repeatedly observed and are determined to be basic characteristics of 'Fisnifire' in combination distinguish this *geranium* as a new and distinct cultivar:

1. brilliant, orange-red, single-type flowers;
2. large inflorescences, and long, dark-red peduncles;
3. dark-green, medium to large leaves with strong zonation;
4. initially fairly compact, later medium to tall sized and well-branched plant habit;
5. about medium spring flowering response; and
6. good rain resistance, robust outdoor plant.

Of the many commercial cultivars known to the present inventor, the most similar in comparison to 'Fisnifire' are the unpatented varieties 'Fisnida' and 'Fispera', and the patented variety 'Waltz' (U.S. Plant Pat. No. 5,931).

In comparison to the orange flowered variety 'Fisnida', 'Fisnifire' has deeper colored, orange-red flowers, somewhat shorter peduncles, and dark green foliage, whereas 'Fisnida' had medium green leaves.

In comparison to 'Fispera', 'Fisnifire' has a roughly similar flower color, but 'Fisnifire' has longer peduncles, and taller plant habit, especially higher foliage canopy.

In comparison to 'Waltz', 'Fisnifire' has a more brilliant flower color, and less deep red peduncles.

BRIEF DESCRIPTION OF THE DRAWING

The accompanying photographic drawing shows typical flower and foliage characteristics of 'Fisnifire' with colors being as true as possible with an illustration of this type. The photographic drawing shows a side perspective view of a flowering potted plant of 'Fisnifire' with leaves, buds and inflorescences.

DETAILED BOTANICAL DESCRIPTION

The measurements were taken in Hillscheid, Germany, in mid May, 11 weeks after planting of rooted cuttings. The plants were growing in 14 cm pots, they had not been pinched.

In the following description, color references are made to The Royal Horticultural Society Color Chart. The color values were determined indoors from plants growing in a green-house in May 2003 in Hillscheid, Germany.

Parentage:
- *Male parent*.—Unpatented, hybrid plant No. 93-0266-7.
- *Female parent*.—'Fishelen' (U.S. Plant Pat. No. 12,727).

Classification: *Pelargonium zonale* L'Héritier (hybrid).
Propagation: Vegetative cuttings.
Inflorescence:
Umbel:
- *Shape*.—Semi-spherical or oval.
- *Average diameter*.—113 mm.
- *Average depth*.—60 mm.
- *Number of flowers per umbel*.—About 30–50.

Peduncle:
- *Peduncle length*.—138 mm.
- *Peduncle diameter*.—4–5 mm.
- *Peduncle color*.—Dark red (greyish-purple group), RHS 184 A.

Pedicel:
- *Pedicel length*.—33 mm in length.
- *Pedicel diameter*.—1.5–2 mm.
- *Pedicel color*.—Mainly greyish-red, RHS 181 A, with RHS 181 C — near lower end.

Corolla:
- *Average diameter*.—52 mm.
- *Depth*.—10–12 mm.
- *Form*.—Single-type.
- *Shape*.—Zygomorphic, with the petals hardly overlapping.
- *Number of petaloids*.—None.

Petals:
- *Number of petals*.—5.
- *Shape of petals*.—Obovate, base acute, upper end is truncate or rounded, margin is entire.
- *Size of petals*.—Upper petals: 28–30 mm long, 17–18 mm wide; lower petals: 26–27 mm long, 20–21 mm wide.
- *Color (general tonality from a distance of three meters)*.—Brilliant, orange-red.
- *Color of upper petals*.—Red, RHS 40 A.
- *Markings of upper petals*.—Fine dark red veins, RHS 53 B, near the base.
- *Color of lower petals*.—Red, RHS 40 A.
- *Markings of lower petals*.—None.
- *Color of lower surface of petals*.—Red, RHS 41 A (upper petals); Red, RHS 43 B (lower petals).

Sepals:
- *Color of sepals*.—Outer surface: greyish-purple, RHS 183 A; inner surface: greyish-red, RHS 178 B.
- *Number of sepals*.—5.
- *Shape of sepals*.—Linear to lanceolate, acute tip, truncate base, surface with very short pubescence, margin entire.
- *Size of sepals*.—15–16 mm long, 5 mm wide for the largest upper sepal, 3–4 mm in width for the other sepals.

Bud (just prior to petals unfolding):
- *Shape*.—Narrow elliptical, asymmetric.
- *Color of sepals*.—Greyish-red, RHS 178 A near the base.
- *Color of petals*.—Red, RHS 43 A.
- *Length*.—19 mm.
- *Width*.—8 mm.

Reproductive organs:
Androecium: 5–7 fertile anthers, moderate pollen, orange-red, RHS 30 A, filaments reddish, RHS 40 A.
Gynoecium: One pistil, style and stigma, red, RHS 44 A, stigma 5–6-lobed stigma, orange-red, RHS N30A.
Fertility/seed set: Moderate, mainly from late summer to fall.
Fruit: Oblong, about 6 mm wide, rostrum (beak) 38–42 mm long.
Seed: Oblong, 4–5 mm long, brown (greyed-orange), RHS 177 B.
Spring flowering response period: In Hillscheid, Germany, in 2003 plants had on average 0.5 flowers opened 8 weeks after planting of rooted cuttings.
Outdoor flower production: Continuously and fairly rich flowering, the flower count in 2003 in Hillscheid, Germany, indicated about 15–20 inflorescences per plant in late summer.
Durability: Good stability of flower color, no fading, relatively good rain resistance, self-cleaning, therefore requiring little care, but not too easily shattering (dropping of petals).
Lastingness of the individual flower: About 7–8 days at 18° C., about 18 days for the umbel.
Fragrance: None.
Plant:
Foliage:
- *Shape*.—Kidney-shaped, most often not flat, but funnel-shaped, with cordate base, with the gap between the lowest lobes open to closed, apex rounded with weak to medium lobes.
- *Margin*.—Bicrenate.
- *Texture*.—Upper surface smooth.
- *Size of leaf*.—89 mm wide, 55 mm long.
- *Color of upper surface*.—Dark green, approximately RHS 137 A.

*Color of zonation*.—Relatively strong brown (greyish-orange), about RHS 166 A.

*Color of lower surface*.—Green, RHS 137 C.

*Petioles*.—75–95 mm long, 3.0 mm diameter, green to weakly brown infused in parts, approximately yellow-green, RHS 143 B to greyish-red, RHS 179 B.

General appearance and form:

*Stem color*.—Greyish-purple, RHS 184 B.

*Internode length*.—10–20 mm.

*Branching pattern*.—5–6 branches.

*Size of plants*.—Height: 11.0 cm, Spread: 26.0 cm (11-week old plants, as described, measured from the top of the soil (base of the main stem) to the surface of the foliage canopy, without inflorescences). Relatively compact during cultivation in the greenhouse, later, outdoors, growing fairly vigorously.

I claim:

1. A new and distinct cultivar of *geranium* plant named 'Fisnifire', as described and illustrated herein.

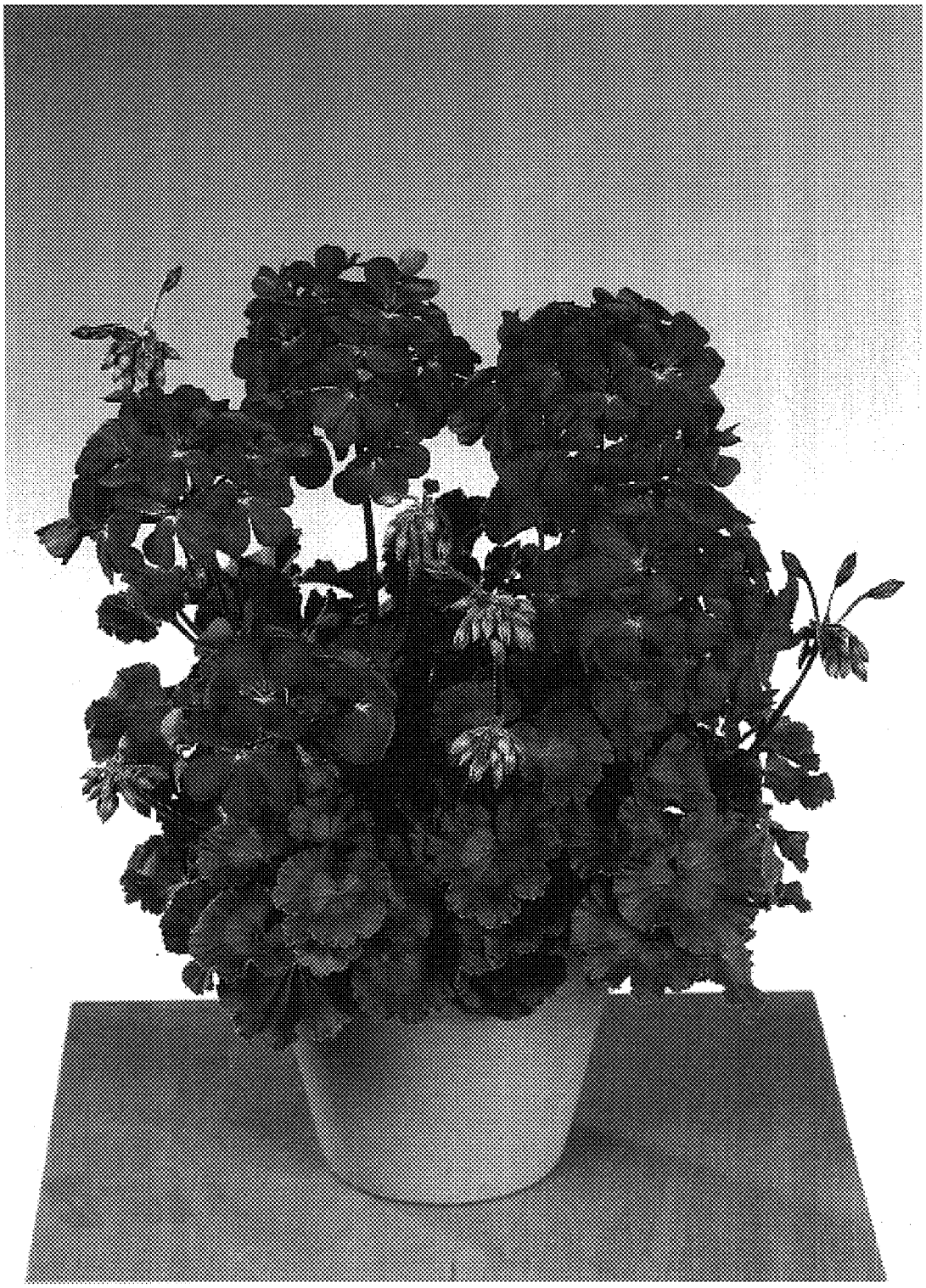

* * * * *